(12) United States Patent
Hsu et al.

(10) Patent No.: US 9,012,849 B2
(45) Date of Patent: Apr. 21, 2015

(54) DIRECT AND QUANTITATIVE BROADBAND ABSORPTANCE SPECTROSCOPY WITH MULTILAYER CANTILEVER PROBES

(71) Applicants: Wei-Chun Hsu, Cambridge, MA (US); Jonathan Kien-Kwok Tong, Cambridge, MA (US); Bolin Liao, Cambridge, MA (US); Brian Burg, Cambridge, MA (US); Gang Chen, Carlisle, MA (US)

(72) Inventors: Wei-Chun Hsu, Cambridge, MA (US); Jonathan Kien-Kwok Tong, Cambridge, MA (US); Bolin Liao, Cambridge, MA (US); Brian Burg, Cambridge, MA (US); Gang Chen, Carlisle, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 65 days.

(21) Appl. No.: 13/937,713

(22) Filed: Jul. 9, 2013

(65) Prior Publication Data
US 2014/0014841 A1    Jan. 16, 2014

Related U.S. Application Data

(60) Provisional application No. 61/669,715, filed on Jul. 10, 2012, provisional application No. 61/681,357, filed on Aug. 9, 2012.

(51) Int. Cl.
| | | |
|---|---|---|
| *G01J 5/02* | (2006.01) | |
| *G01J 3/45* | (2006.01) | |
| *G01T 1/36* | (2006.01) | |
| *G01N 21/17* | (2006.01) | |
| *G01N 21/3563* | (2014.01) | |

(52) U.S. Cl.
CPC ... *G01J 3/45* (2013.01); *G01T 1/36* (2013.01); *G01N 21/1702* (2013.01); *G01N 21/171* (2013.01); *G01N 21/3563* (2013.01)

(58) Field of Classification Search
CPC ..................................... G01J 3/45; G01T 1/36
USPC .................................... 250/339.12; 356/497
See application file for complete search history.

(56) References Cited

U.S. PATENT DOCUMENTS

| | | |
|---|---|---|
| 5,060,248 A | 10/1991 | Dumoulin |
| 5,285,261 A | 2/1994 | Dumoulin |

(Continued)

FOREIGN PATENT DOCUMENTS

WO    WO 2011007168 A2 *    1/2011

OTHER PUBLICATIONS

Hsu et al., "Direct and quantitative broadband absorptance spectroscopy on small objects using Fourier transform infrared spectrometer and bilayer cantilever probes" Applied Physics Letters 102, 051901, 2013, pp. 051901-1-051901-5.

(Continued)

*Primary Examiner* — David Porta
*Assistant Examiner* — Abra Fein
(74) *Attorney, Agent, or Firm* — Gesmer Updegrove LLP

(57) ABSTRACT

A system for measuring the absorption spectrum of a sample is provided that includes a broadband light source that produces broadband light defined within a range of an absorptance spectrum. An interferometer modulates the intensity of the broadband light source for a range of modulation frequencies. A bi-layer cantilever probe arm is thermally connected to a sample arm having at most two layers of materials. The broadband light modulated by the interferometer is directed towards the sample and absorbed by the sample and converted into heat, which causes a temperature rise and bending of the bi-layer cantilever probe arm. A detector mechanism measures and records the deflection of the probe arm so as to obtain the absorptance spectrum of the sample.

24 Claims, 12 Drawing Sheets

(56) References Cited

U.S. PATENT DOCUMENTS

| | | | |
|---|---|---|---|
| 5,737,086 | A | 4/1998 | Gerber et al. |
| 8,242,448 | B2 | 8/2012 | Prater et al. |
| 2005/0052656 | A1* | 3/2005 | Lindner et al. .......... 356/497 |
| 2010/0033723 | A1 | 2/2010 | Thundat et al. |
| 2010/0282969 | A1 | 11/2010 | Frank et al. |
| 2011/0139990 | A1 | 6/2011 | Xie et al. |
| 2012/0194823 | A1 | 8/2012 | Moore et al. |

OTHER PUBLICATIONS

Arakawa et al., "Detection of anthrax simulants with microcalorimetric spectroscopy: *Bacillus subtilis* and *Bacillus cereus* spores" Applied Optics, Apr. 1, 2003, vol. 42, No. 10, pp. 1757-1762.

Skvortsov et al., "Application of laser photothernal spectroscopy for standoff detection of trace explosive residues on surfaces" Quantum Electronics 40 (7) 2010, pp. 565-589.

Gotoh, "Photothermal technique using individual cantilevers for quality monitoring in thin film devices" Review of Scientific Instruments 80, 2009, 074902-1-074902-4.

International Search Authority and Written Opinion mailed on Oct. 28, 2013, in connection with corresponding PCT Application No. PCT/US2013/049705.

Tetard et al., "Optomechanical spectroscopy with broadband interferometric and quantum cascade laser sources" Optics Letters, Aug. 15, 2011, vol. 36, No. 16, pp. 3251-3253.

* cited by examiner

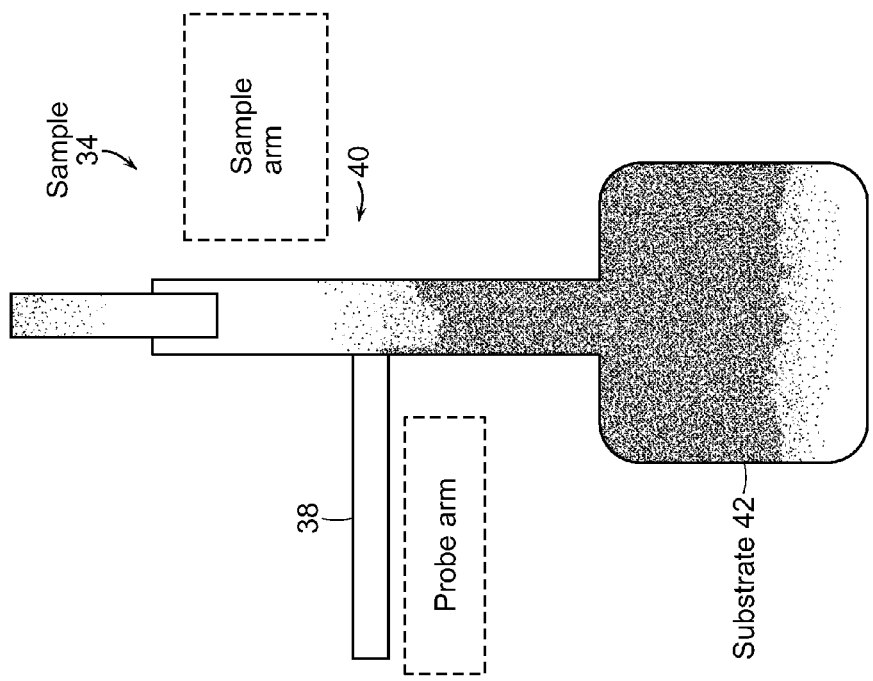
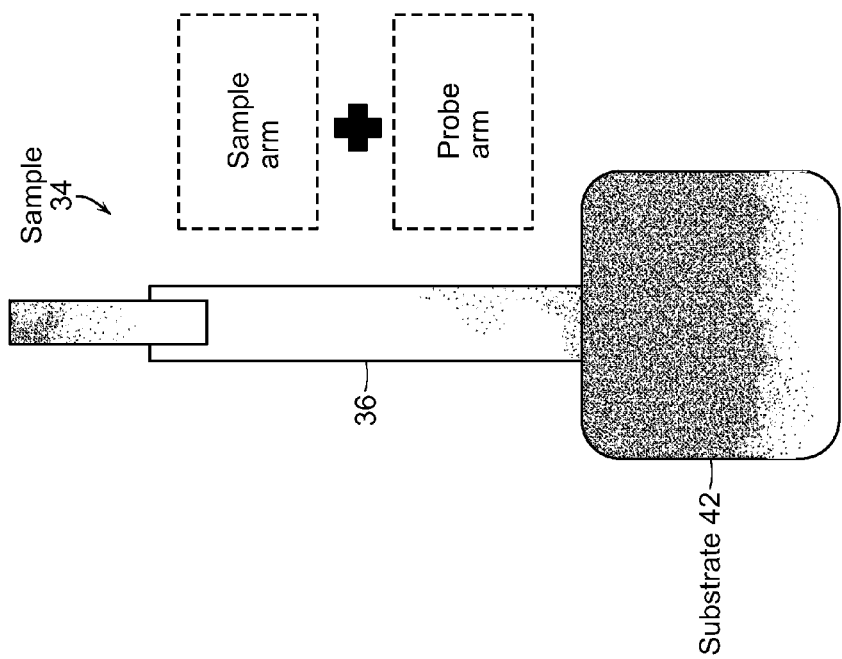

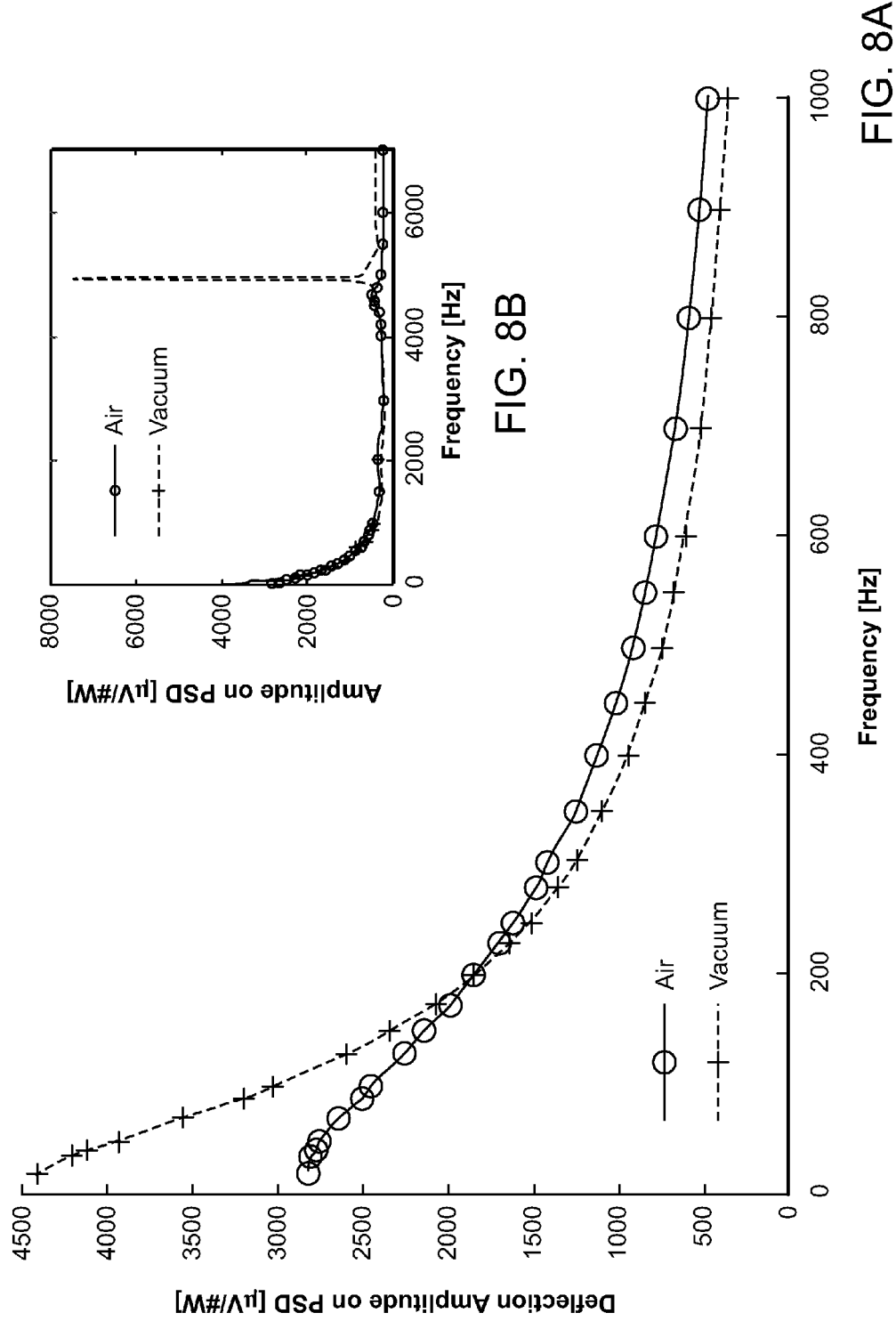

DIRECT AND QUANTITATIVE BROADBAND ABSORPTANCE SPECTROSCOPY WITH MULTILAYER CANTILEVER PROBES

PRIORITY INFORMATION

This application claims priority from provisional application Ser. No. 61/669,715 filed Jul. 10, 2012 and provisional application Ser. No. 61/681,357 filed Aug. 9, 2012, which are incorporated herein by reference in their entireties.

This invention was made with government support under Grant No. DE-FG02-02ER45977 awarded by the Department of Energy. The government has certain rights in the invention.

BACKGROUND OF THE INVENTION

The invention is related to the field of spectroscopy, and in particular to a direct and quantitative broadband absorptance spectroscopy technique using multilayer cantilever probes.

Fourier transform infrared (FTIR) and Fourier transform visible (FTVIS) spectroscopy, referred to as Fourier Transform Spectroscopy (FTS) in general, are well-known techniques to measure the optical properties of materials. By using different sample stages, FTIR and FTVIS systems can measure the transmittance and reflectance spectra of a sample in a single scan. Compared to dispersive spectrometers, FTIR and FTVIS have several important advantages. First, the multiplex advantage (or Fellgett advantage) implies that FTIR and FTVIS systems can simultaneously measure all wavelengths in the illumination source, thus a complete spectrum can be collected in a single scan faster than for conventional dispersive spectrometers. Second, the throughput advantage (or Jacquinot advantage) refers to the higher energy throughput of FTIR and FTVIS systems compared to dispersive spectrometers which results in a higher signal-to-noise ratio for the same spectral resolution. Third, since FTIR and FTVIS system use an interferometer to modulate the spectrum instead of prisms or gratings, stray light is negligible unlike in dispersive spectrometers.

Traditional methods to measure an absorption spectrum, including FTIR and FTVIS, are typically indirect, in the sense that the absorption spectrum of materials can only be calculated after measuring the transmittance and reflectance spectrum. This approach inevitably introduces uncertainties and errors in the result. For bulk materials, indirect methods are usually adequate to determine absorption characteristics, qualitatively or even quantitatively. For small samples on the micro or nanometer scale, however, it is difficult to use the FTS method to characterize the respective absorption spectrum, since the light scattered by the sample can cause disproportionally large errors.

An example of a direct absorptance measurement method is the photoacoustic method in which heat absorbed by the sample generates an acoustic wave that propagates in a surrounding gas. This acoustic wave is subsequently picked up by an acoustic detector. The photoacoustic method, however, is limited to macroscopic objects due to a lower signal-to-noise ratio for microscopic objects. Another commercial instrument for direct absorptance measurements is the Nano IR spectroscopy technique from Anasys Instruments, which detects absorbed power directly by measuring the thermal expansion using the tip of a micro-fabricated cantilever. This method is able to probe local areas equivalent to the size of the tip.

Micro-fabricated bilayer cantilevers have been used as direct and quantitative thermal sensors with an ultra-high power resolution. When the cantilever consists of multiple layers of materials with different thermal expansion coefficients, it bends under the influence of temperature change. The simplest case is a bilayer cantilever, which was used in the development of this platform. As photothermal sensors (or a heat flux sensors), micro-cantilevers have reported sensitivities as low as 4 pW. After carrying out appropriate calibration, the cantilevers can be used to extract quantitative data. Bilayer cantilevers have been used to measure the thermal conductance of thin films, near-field thermal radiation, the absorptivity of a thin gold film, the absorption of a few isolated chemical materials and the thermal conductivity of polyethylene nanofibers.

SUMMARY OF THE INVENTION

According to one aspect of the invention, there is provided a system for measuring the absorption spectrum of a sample. The system includes a broadband light source that produces broadband light defined within a range of an absorption spectrum. An interferometer modulates the intensity of the broadband light source for a range of modulation frequencies. A bi-layer cantilever probe arm is thermally connected to a sample arm having a plurality of layers of materials. The broadband light modulated by the interferometer is directed towards the sample and absorbed by the sample and converted into heat, which causes a temperature rise and bending of the bi-layer cantilever probe arm. A detector mechanism measures and records the deflection of the probe arm so as to obtain the absorption spectrum of the sample.

According to another aspect of the invention, there is provided a method of measuring the absorption spectrum of a sample. The method includes producing broadband light defined within a range of an absorption spectrum using a broadband light source. Also, the method includes modulating the intensity of the broadband light source for a range of modulation frequencies using an interferometer. A bi-layer cantilever probe arm is provided that is thermally connected to a sample arm having a plurality layers of materials The broadband light modulated by the interferometer is directed towards the sample and absorbed by the sample and converted into heat, which causes a temperature rise and bending of the bi-layer cantilever probe arm. Moreover, the method includes measuring and recording the deflection of the probe arm so as to obtain the absorption spectrum of the sample.

BRIEF DESCRIPTION OF THE DRAWINGS

FIGS. 2A-2B are schematic diagram of decoupled cantilever arms used in accordance with the invention;

FIGS. 8A-8B are graphs illustrating the frequency response of a rectangular Si/Al cantilever.

DETAILED DESCRIPTION OF THE INVENTION

The invention involves a platform that integrates a bilayer cantilever with a Fourier Transform Spectrometer, to enable direct absorptance measurements of small samples, either qualitatively or quantitatively. The system maintains the advantages of FTS systems, specifically the multiplex and throughput advantage, but in addition, enables direct land quantitative absorption measurements of small samples with high sensitivity.

Figure 1:
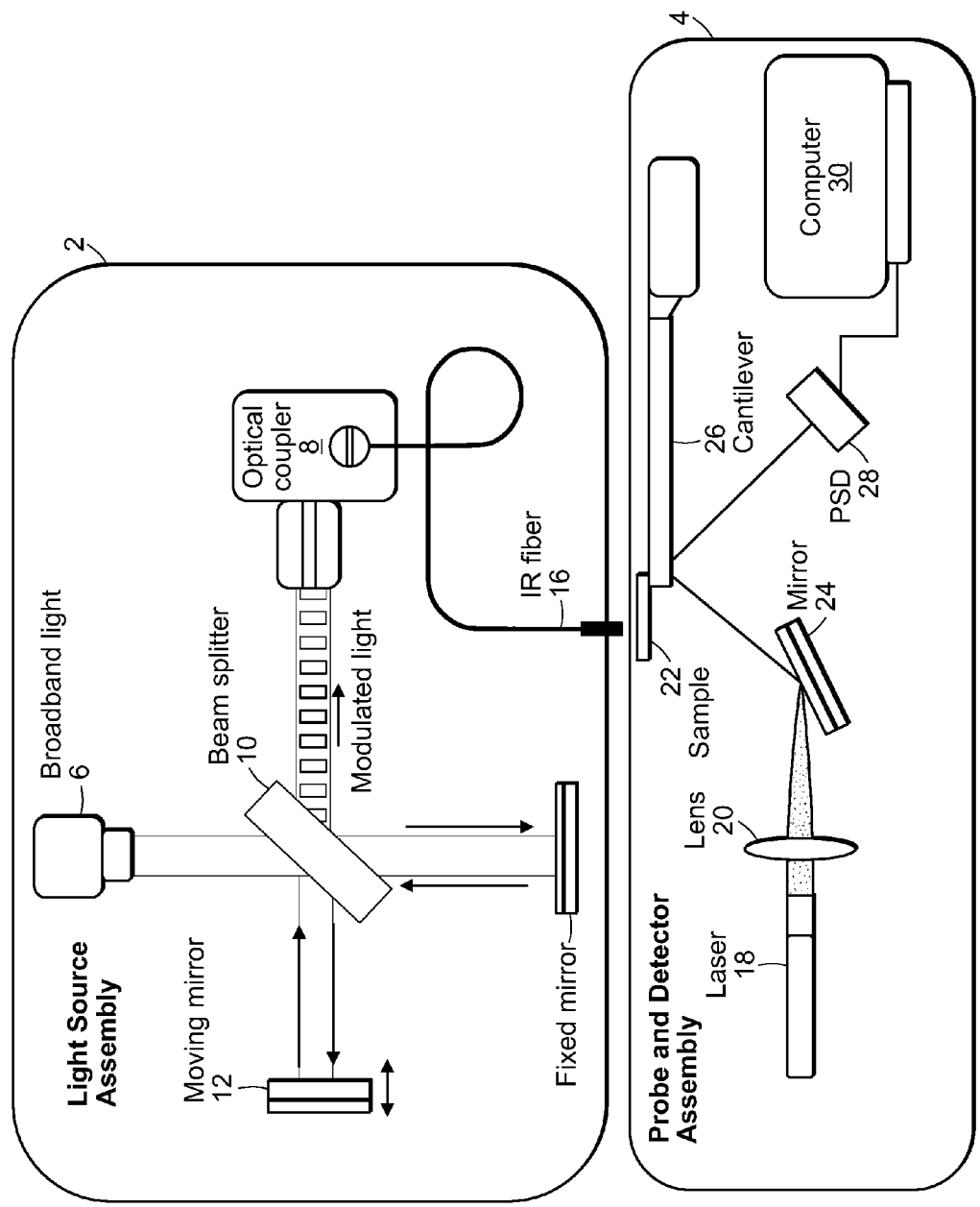
FIG. 1 is a schematic diagram of the inventive measurement system.

FIG. 1 is a schematic diagram illustrating the inventive platform having a light source assembly 2 and a probe and detector assembly 4. The light source assembly 2 includes a broadband light source 6, a beamsplitter 10, an optical coupler 8, a movable mirror 12, a fixed 14, and an IR fiber 16. The probe and detector assembly 4 combines the sample 22, a laser 18 and lens structure 20, a mirror 24, a bilayer cantilever probe 26, a Position Sensitive Detector (PSD) 28, and a computer 30 to carry out Fourier transform analysis. The broadband light source dictates the spectral range of the absorption measurement and can conceivably cover any region, e.g. ranging from infrared to visible, or ultraviolet. The interferometer modulates the intensity of the broadband light source, providing a means of spectrally resolving electromagnetic radiation in the terahertz regime.

The interferometer modulates the intensity of the broadband light source, providing a means of spectrally resolving electromagnetic radiation in the terahertz regime. Different types of interferometers can be used including a Michelson interferometer, Mach-Zender interferometer, Sagnac interferometer, Bath interferometer, or Fabry-Perot interferometer. The bilayer cantilever functions as the principle thermal sensor in this system. It should be emphasized that the cantilever can be composed of multiple layers and still be used as a heat flux probe. The bilayer cantilever (the probe arm) is thermally linked to the sample holder (the sample arm), or can serve as the sample holder itself, as shown in FIGS. 2A and 2B. In particular, FIG. 2A shows the bilayer cantilever 36 functions as both the sample holder and the probe while FIG. 2B shows the sample arm 40 is separated from the probe arm 38 (the bilayer cantilever). Note the sample arms 36, 40 are coupled to substrate structure 42. In general, when the sample absorbs light, the energy is then conducted along the cantilever as heat. This results in a temperature change which causes the cantilever to bend due to thermal expansion.

The deflection of the cantilever is typically measured optically using a laser reflected off the cantilever onto a PSD. Other means of measuring the deflection of the cantilever include capacitance or tunneling schemes. These methods, however, tend to be less sensitive. Generally, the cantilever probe is multi-layer, and, at least, two layers of the cantilever that bends due to the temperature change can be used as the heat flux probe. The cantilever deflection signal is ultimately analyzed using Fourier transform analysis to extract the absorption properties of the sample.

To demonstrate the feasibility of the concept, a FTIR system with a Michelson interferometer and a silicon/aluminum bilayer cantilever are used together. The light source consists of a wire coil that operates at 1100K, covering the wavelength range from near-infrared (2 μm) to mid-infrared (~20 μm). The operating principle of the Michelson interferometer is as follows. When the light beam hits the beam splitter 10, half of the light is transmitted and the other half is reflected. The transmitted light is directed toward a fixed mirror 14, while the reflected light is directed towards a moveable mirror 12. The mirrors then reflect the two light beams back to the beam splitter 10 resulting in interference. This interference is dependent on the difference in the optical path lengths of the two beams. If the distances from the beam splitter 10 to the moveable mirror 12 and the fixed mirror 14 are equal (or integer multiples of a particular wavelength), the two beams constructively interfere.

However, if the moveable mirror 12 is shifted by half the wavelength, the two beams will destructively interfere. Therefore, as this mirror is continually moved, it will transition between points of constructive and destructive interference. The resulting modulated light in FIG. 1 will thus transition from a maximum to minimum. The intensity of each wavelength, λ, or wavenumber, η, is modulated by a specific frequency, f, dependent on the velocity of the moveable mirror, v. Consequently, each wavelength has a different periodicity created by the mirror motion and the modulated periodic frequency with respect to its corresponding wavelength follows the relation:

$$f = \frac{2v}{\lambda} = 2v\eta \qquad (1)$$

Figure 3:
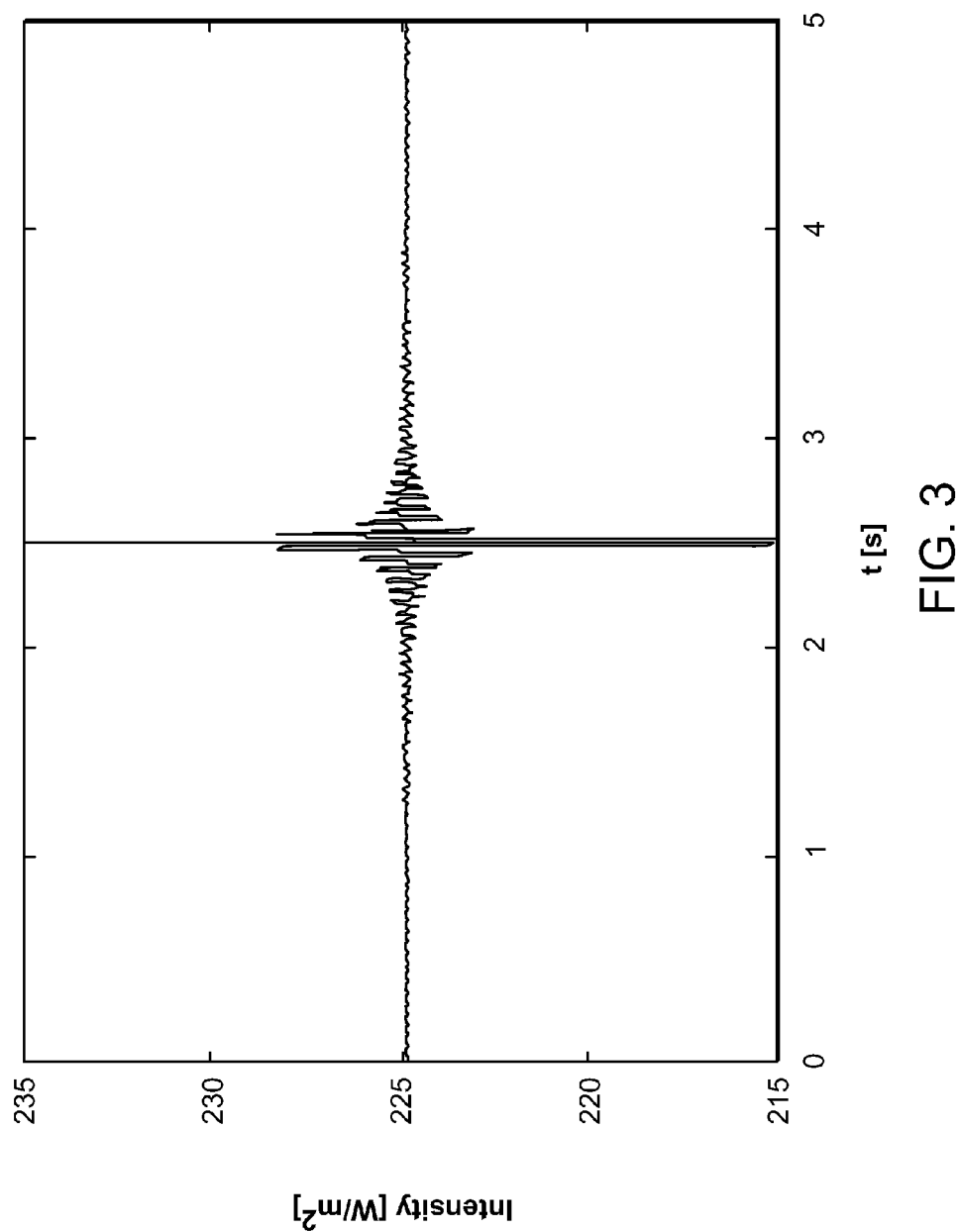
FIG. 3 is a graph illustrating a simulated interferogram pattern from a Michelson interferometer.

Since the light source is broadband, the intensity as a function of time forms an interferogram pattern, which is shown in FIG. 3. In a conventional FTIR system, light coming out of the Michelson interferometer is directed onto the sample. Either transmitted or reflected light from the sample is then recorded in the detector. By measuring the reflected light and transmitted light, and after comparison with a reference sample, the sample reflectance or transmittance can be determined.

In the proposed system, the modulated light from the Michelson interferometer is coupled into a Polycrystalline Infra-Red (PIR) fiber by an optical fiber coupler and is directed toward the sample. The sample is attached on a sample stage that is thermally linked to the bilayer.

Figure 4A:
FIGS. 4A-4B are schematic diagrams illustrating bending of a bilayer cantilever beam due to a temperature change.
Figure 4B:
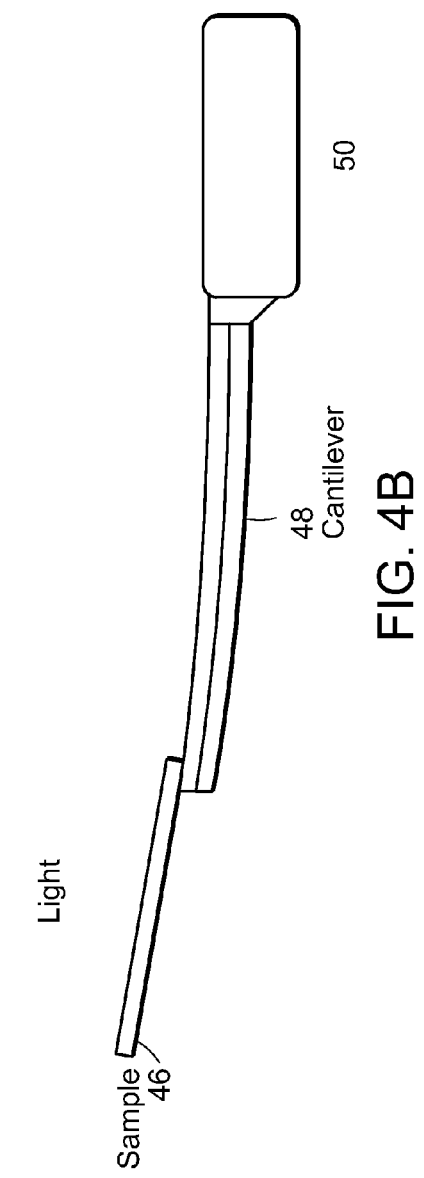

The bilayer cantilever is used as both the probe and the sample stage to measure the optical absorptance of the sample directly and quantitatively. FIGS. 4A-4B illustrates how the cantilever 48, made of two material layers with different coefficients of thermal expansion, behaves when light is absorbed. When the sample 46 absorbs light, the energy will conduct along the sample 46 and the cantilever 48 towards the base 50 of the cantilever 48 via heat conduction, as shown in FIG. 4A. This will cause the temperature of the cantilever 48 to rise. Since the two layers of the cantilever 48 have different thermal expansion coefficients, the temperature rise will cause the cantilever 48 to bend, as shown in FIG. 4B.

For quantitative spectra measurements, the system requires four calibrations: the background spectrum calibration, beam intensity profile calibration, frequency response calibration and power calibration.

Figure 5:
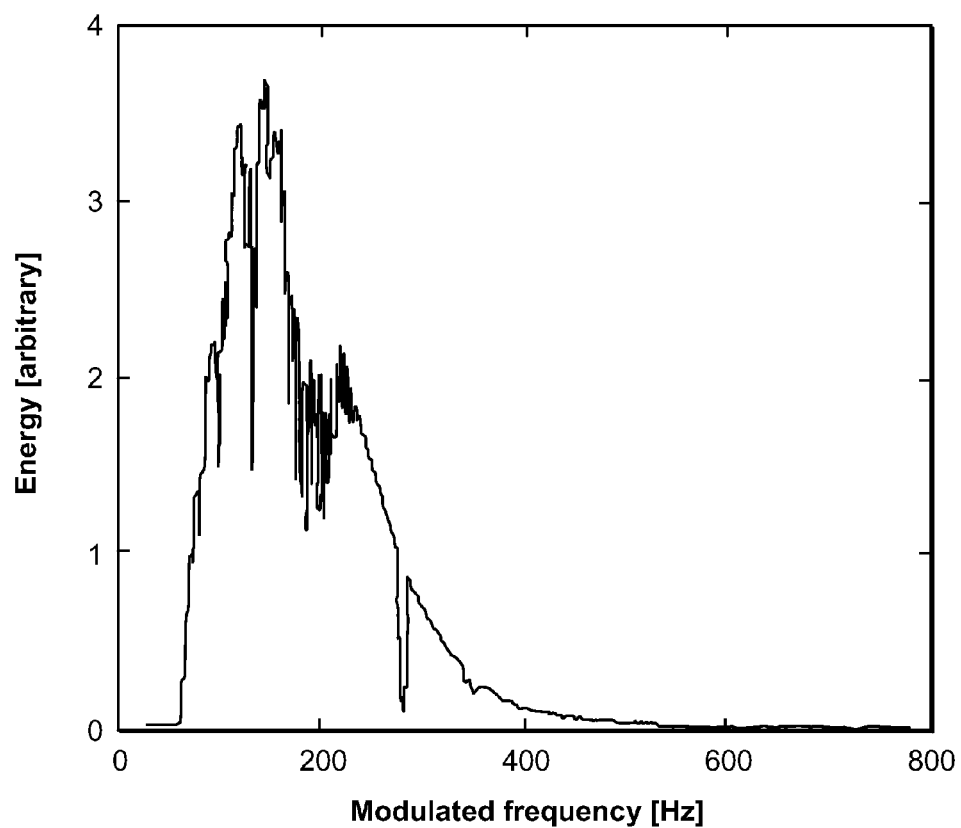
FIG. 5 is a graph illustrating a background spectrum representing the incident input intensity spectrum on a cantilever.

First, the background spectrum calibration is needed to calibrate variations In the spectral intensity of the light source as well as atmospheric absorption. The incident input power spectrum, shown in FIG. 5, is measured by a FTIR system (PerkinElmer Spectrum GX) after the PIR fiber. Note that the x axis has been changed from wavenumber to modulated frequency using Eq. 1. The absorptance spectrum can then be calculated by dividing the absorbed power spectrum with the incident input power spectrum.

Figure 6:
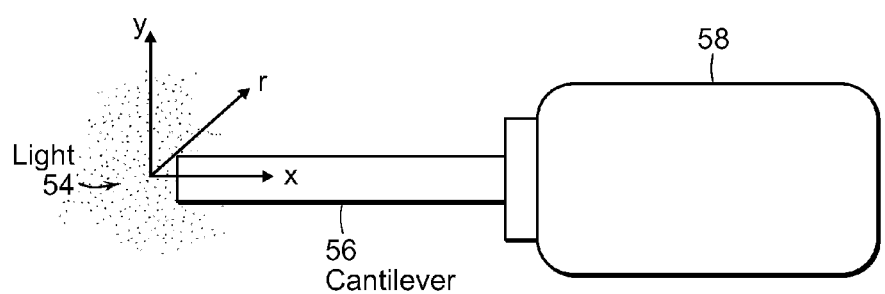
FIG. 6 is a schematic diagram illustrating a beam spot formed in accordance with the invention.

Second, the beam intensity profile calibration takes into account the nonuniform intensity output profile from the PIR fiber using a photodetecor. Since the incident input power varies with position, the intensity profile and the alignment of the sample to the PIR fiber must be known with a high degree of precision. Illustrating this point is a schematic of a typical beam spot 54 incident on a portion of a cantilever 56, shown in FIG. 6. The beam spot 54 from a PIR fiber 58 is typically larger than the cantilever 56. The beam intensity profile can be measured using a simple knife-edge technique or approximated by solving Maxwell's equations.

Figure 7A:
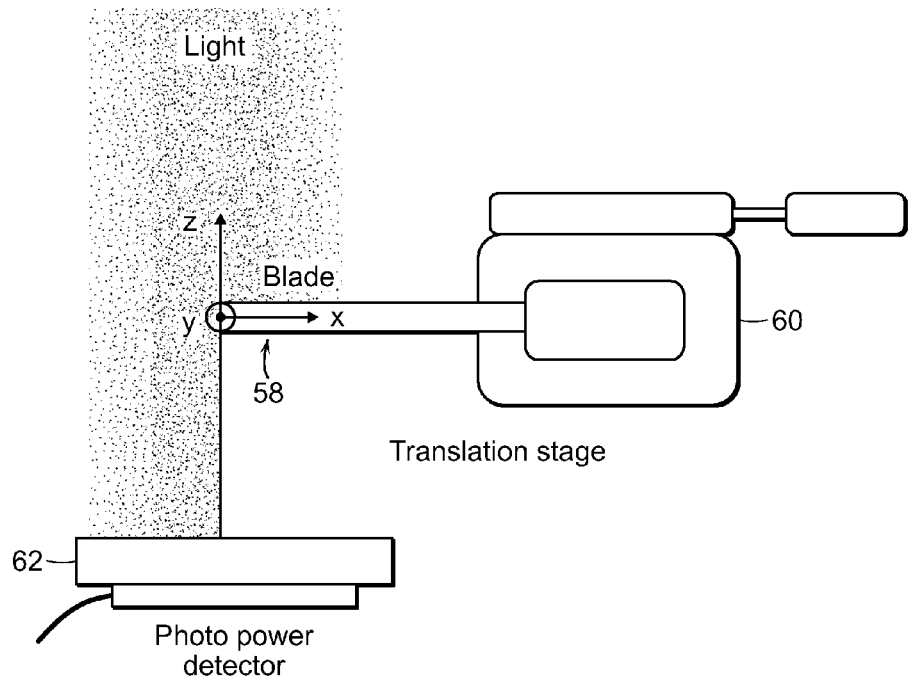
FIGS. 7A-7B demonstrate a schematic diagram and beam intensity profile of the knife-edge technique used by the invention.
Figure 7B:
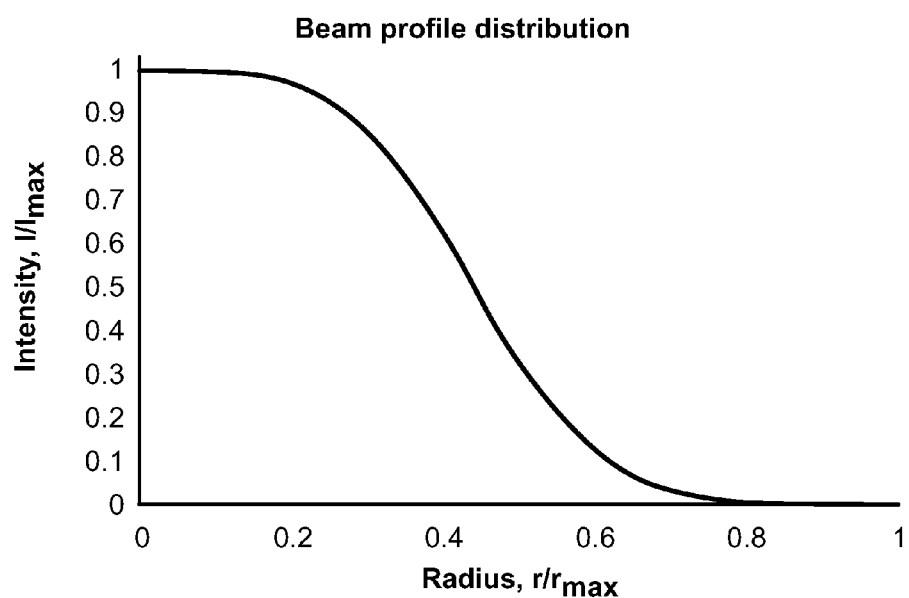

In essence, a blade 58 with a well-defined edge is inserted between the PIR fiber 60 and a photodetector 62, as shown in FIG. 7A, and moved in incremental steps until the beam is fully blocked. The photodetector 62 records the power at each step. The power measured at each step represents an integrated beam intensity profile. Generally, a Gaussian profile is used to fit the beam profile distribution, as shown in FIG. 7B. Of course, one could also design optical component so that the beam has a different profile, and in fact, preferably a uniform profile.

The frequency response calibration accounts for the phase delay of the periodic heat input conducting through the cantilever at the different light modulation frequencies. This phase delay, which is dependent on the thermal diffusivity of the cantilever, will lead to a reduction of the deflection amplitude at higher modulation frequencies. To characterize the frequency response of the cantilever, a DC light source with a constant intensity is modulated using a mechanical chopper with a 50% duty cycle. FIGS. 8A-8B show the frequency response data measured for a Si/Al cantilever in both air and vacuum. Each data point represents the vibration amplitude measured by the PSD at the chosen modulating frequency. The signal-to-noise ratio can be enhanced in vacuum as convection losses become negligible. Under vacuum, a peak resonance can be observed around 4900 Hz, as shown in FIG. 8B. This corresponds to the resonance frequency of the cantilever, and it is a confirmation of the cantilever-type probe.

More importantly, it can be observed that the amplitude decreases with increasing frequency. Therefore, to maintain a measurable signal while avoiding low frequency noise, the working region is chosen to be in the range of 30-1000 Hz, illustrated in FIG. 8A. Using this data, the cantilever deflection amplitude reduction induced by the periodic heat input over the entire range of modulated incident light frequencies from the interferometer can be accounted for.

Figure 9:
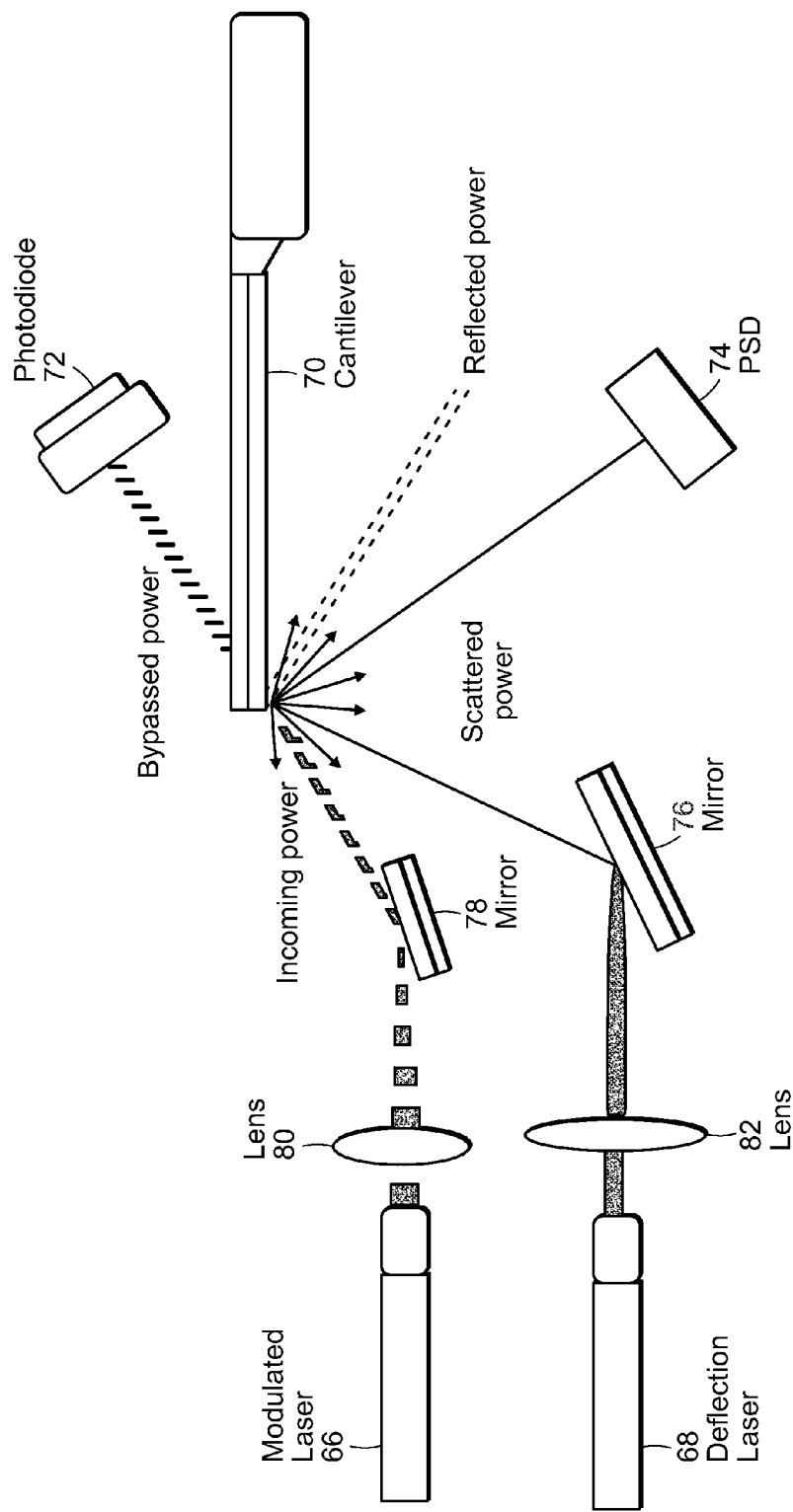
FIG. 9 is a schematic diagram illustrating a system configuration used in the power calibration.

Finally, the power calibration correlates the oscillating amplitude measured by the PSD to the absolute power absorbed by the cantilever. Three steps are required as shown in FIG. 9. First, the incident power on the cantilever 70 is obtained by subtracting the bypassed power, using a modulated laser 66 and lens structure 80, from the incoming power using a deflection laser 68 and lens structure 82. The bypassed power and incoming power are measured using a photodiode 72 as FIG. 9. The PSD 74 collects remnants of scattered power. Second, the absorptance of the metal film, aluminum in this case, is measured using a conventional spectrometer by depositing metal on a Si wafer using the same PVD process as for the cantilever 70. The metal is optically thick so that substrate effects are negligible.

After measuring the absorptance, the absorbed power on the cantilever 70 can be calculated by multiplying the absorptance with the incident power. Note that the absorbed power is obtained in this manner because the scattered power is difficult to determine. Third, an arbitrary modulation frequency is chosen as reference for the absolute power absorbed in the frequency response of FIGS. 8A-8B. The deflection amplitude on the PSD then correlates to the known absorbed power on the cantilever at the given frequency. Subsequently, correction factors for absorbed power versus deflection amplitudes at other frequencies can be determined using the frequency response data from the previous calibration, and hence, the incident spectrum can be converted from the cantilever deflection amplitude to absorbed power.

To sum up, the calibrations can be described as a product of four factors as follow:

$$f_T(\vec{r},\omega) = f_B(\omega) \cdot f_I(\vec{r}) \cdot f_F(\omega) \cdot f_p \quad (2)$$

where $f_T(\vec{r},\omega)$ is the total calibration factor, $f_B(\omega)$ is the background calibration factor, $f_I(\vec{r})$ is the beam intensity profile calibration factor, $f_F(\omega)$ is the frequency calibration factor, and $f_p$ is the power calibration factor, $\vec{r}$ is the spatial position, and $\omega$ is the modulation frequency. The variables $f_B(\omega)$ and $f_F(\omega)$ are frequency dependent, and $f_I(\vec{r})$ is space dependent. Once these four calibrations are measured, quantitative measurements can be carried out by multiplying these factors with the raw data.

The periodic light input from the interferometer on the cantilever changes the absorbed power in the sample with respect to time, and consequently the temperature of the cantilever varies in time. Hence, the bilayer cantilever will deflect in an oscillating pattern, and the laser beam reflected on the metallic side of the cantilever to a PSD is used to measure the deflection pattern of the cantilever.

Figure 10:
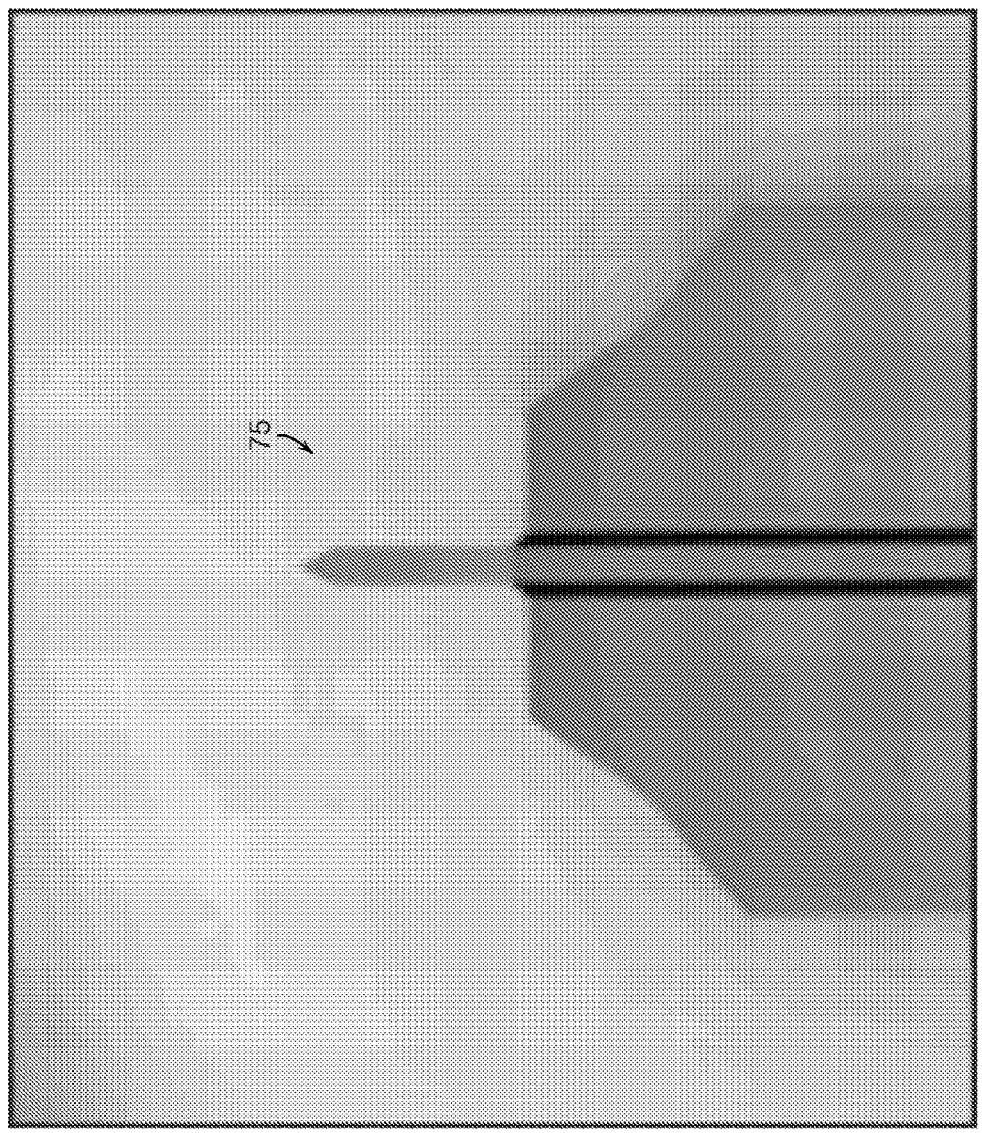
FIG. 10 is schematic diagram illustrating the top view of a silicon cantilever beam.
Figure 11A:
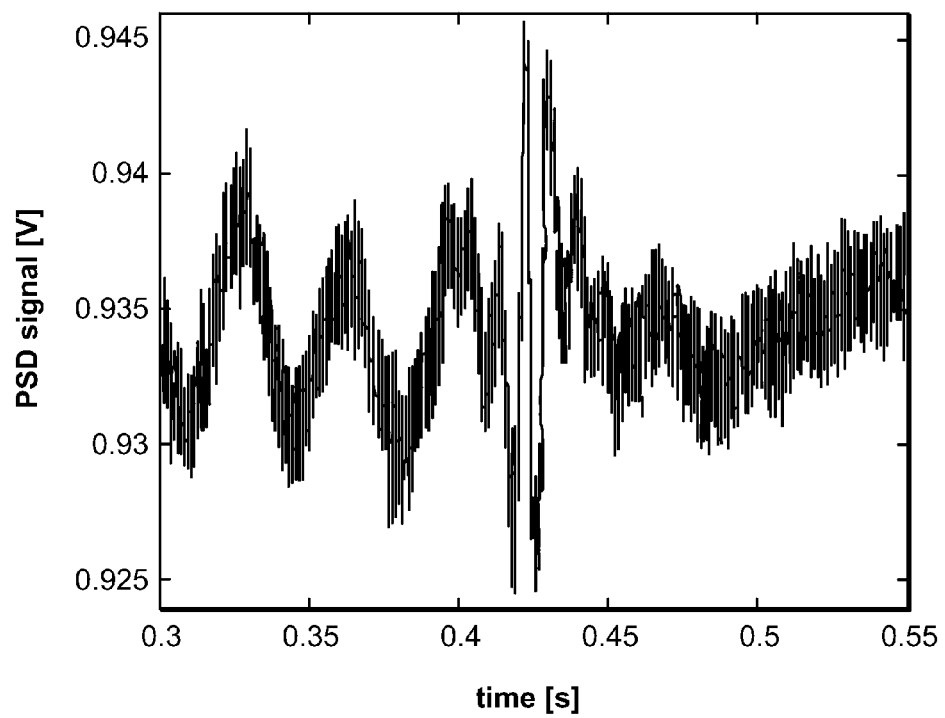
FIGS. 11A-11B are graphs illustrating the signal recorded on a Positive Sensitive Detector (PSD) from the deflection signal of the Si/Al cantilever beam.
Figure 11B:
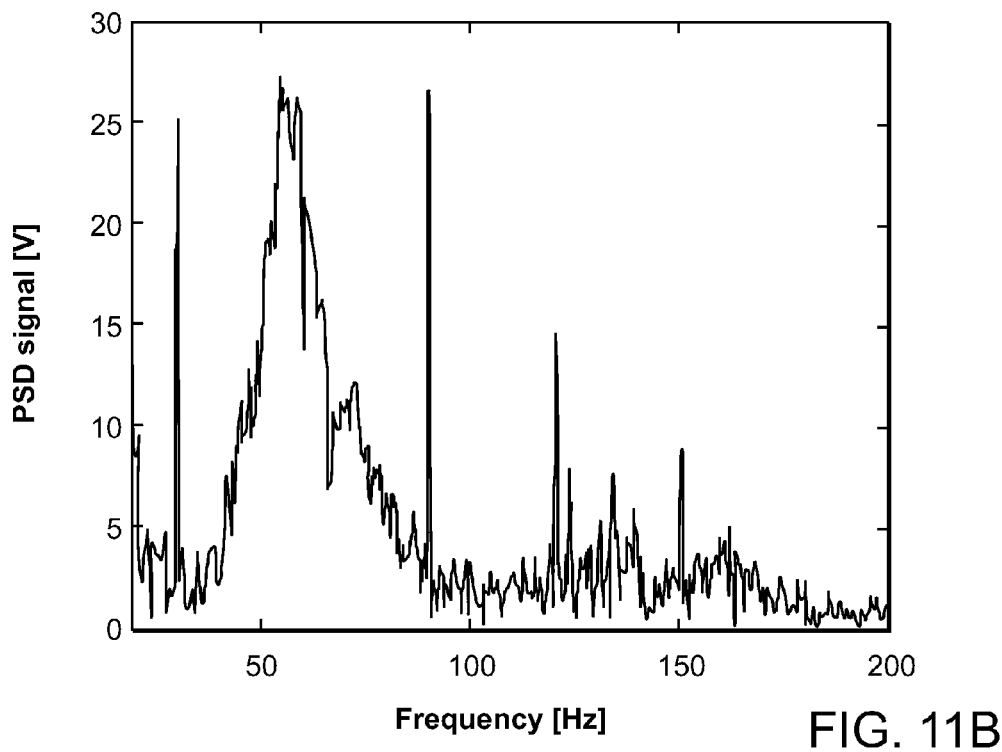

A silicon/aluminum cantilever is chosen for demonstration purposes. Physical vapor deposition (PVD) is used to deposit an aluminum layer of 250 nm onto the 111 m thick commercially available silicon cantilever 75, as shown in FIG. 10. FIGS. 11A-11B show the deflection signal from a Si/Al cantilever during a typical measurement. The modulated light is incident on the silicon layer, and FIG. 11A displays the oscillating signal of the cantilever deflection captured by the PSD. Since the modulated light intensity combines components of many frequencies, an interferogram-patterned signal can be observed in the time domain. Taking the Fourier transform of the signal in FIG. 11A generates the spectral component of the signal, more precisely the spectrum of absorbed power. Following the principles of the Michelson interferometer, frequencies of FIG. 11B can be converted to their corresponding wavelengths.

Figure 12:
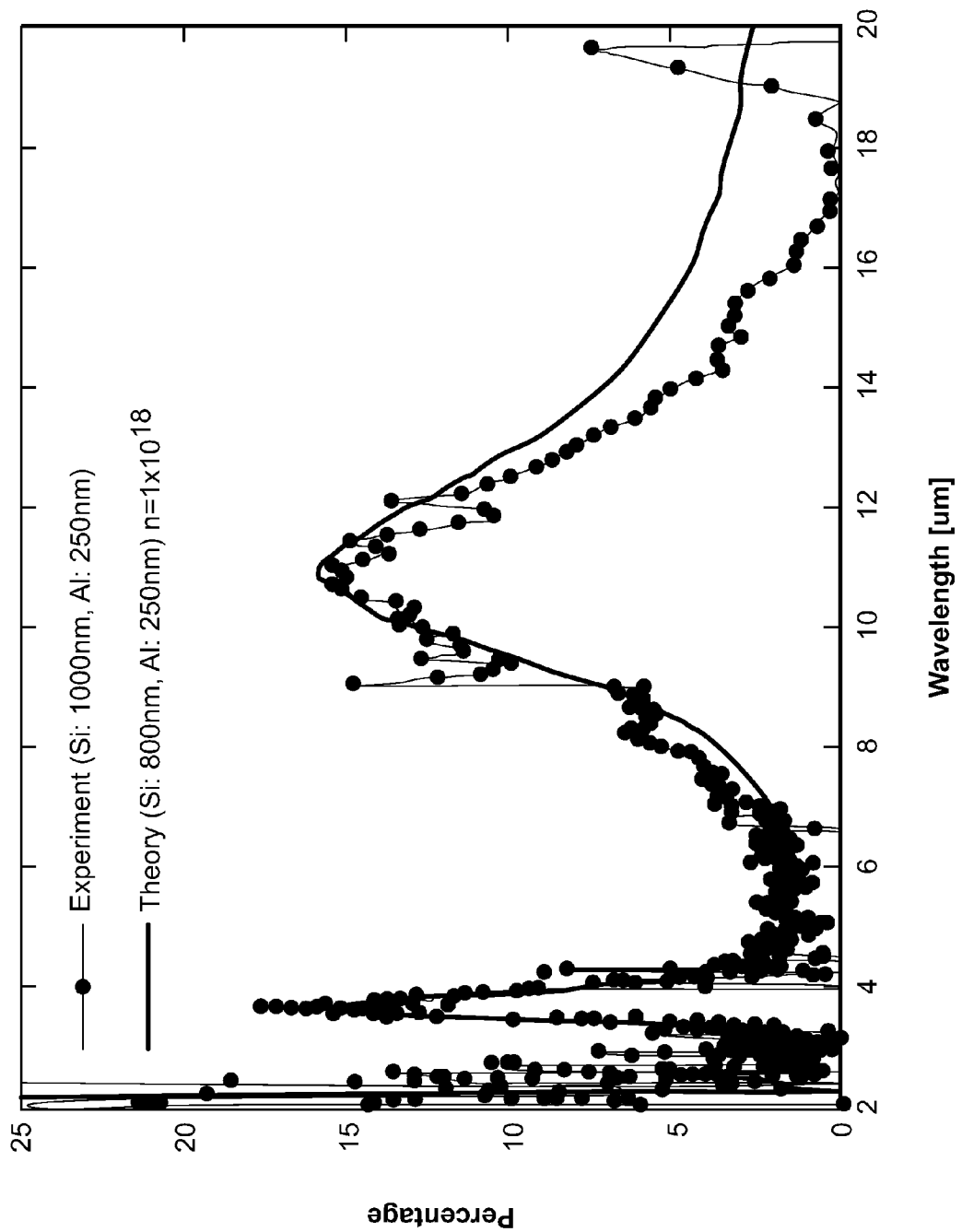
FIG. 12 is a graph illustrating the absorptance spectrum of a Si/Al cantilever fitted to theory.

At present, the beam intensity profile calibration and the power calibration are still a work in progress. These two calibrations are needed in order to extract quantitative data from the system. However, these calibrations can typically result in frequency independent proportionality factors when applied to experimental data. Therefore, from the background spectrum calibration and the frequency response calibration, the system can still yield accurate qualitative data. For the Si/Al cantilever, fitted experimental results have been demonstrated to match well with theory, as shown in FIG. 12. The theoretical results were calculated using the transfer matrix method with the geometric dimensions previously specified, bulk properties of aluminum, and n-type silicon with a dopant concentration of $5 \times 10^{18}$ [$cm^{-3}$]. The variation of thickness variation of the silicon layer provided by ranges from 500 nm to 2500 nm, and 800 nm is used to fit the experimental results. Note that the x axis in FIG. 12 was changed from frequency to wavelength using Eq. (1).

Figure 13:
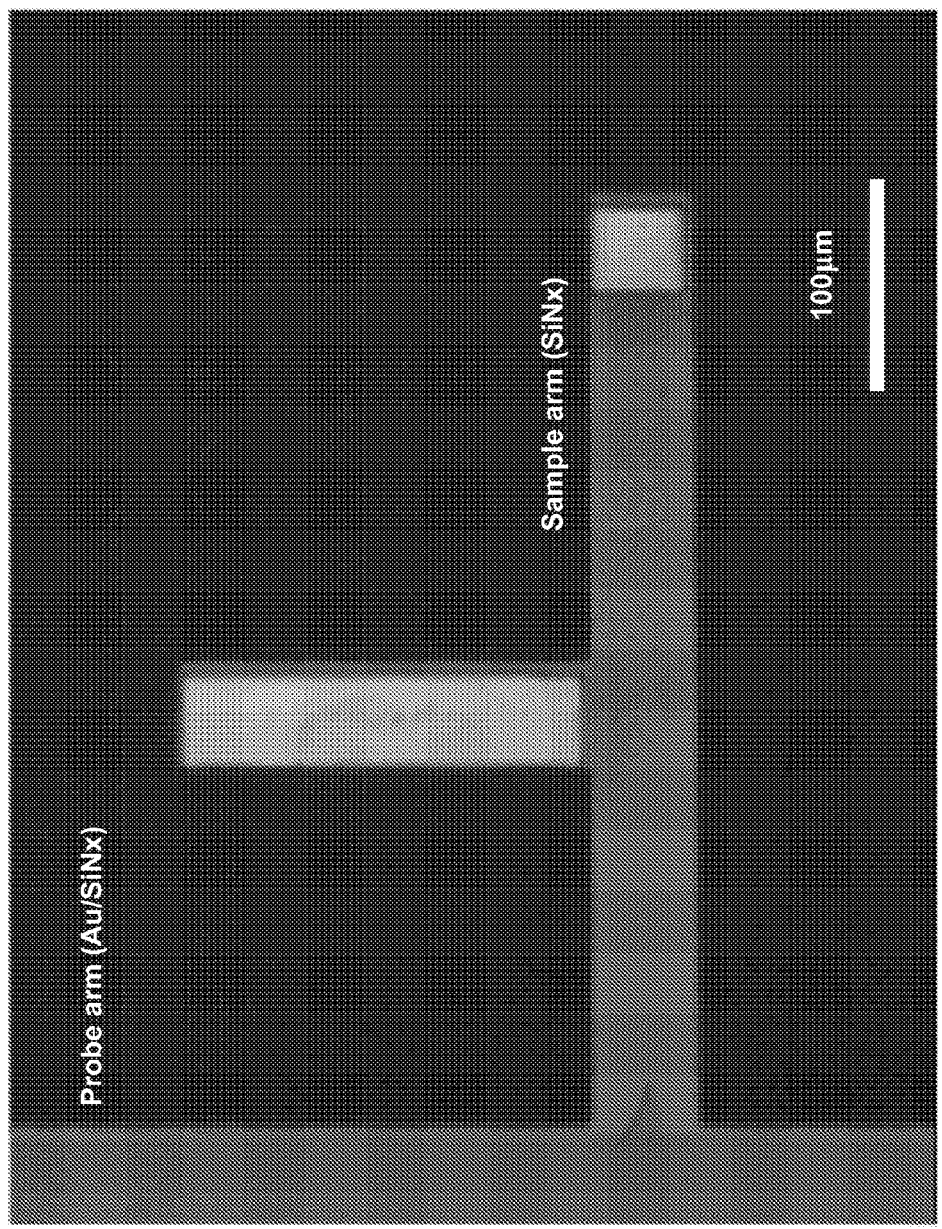
FIG. 13 is a SEM diagram illustrating a SiNx/Au bi-arm cantilever sensor used in accordance in the invention.

Experimental results presented so far are based on commercially available cantilevers. It should be emphasized that different variations of the cantilever-based sensor can also be used in this system. For example, a new structural design, which consists of a bi-arm cantilever platform that decouples the sample stage and the detector 16 was recently disclosed. FIG. 13 shows an optical microscope image of this bi-arm cantilever. The probe arm is composed of a silicon nitride (SiNx) substrate with an Au coating. The sample arm is made up of only SiNx with an Au reflective coating at its tip for sensing and optical heating. This coating does not affect the deflection response of the detector arm.

There are three reasons for decoupling the detector arm and the sample arm. First, by isolating the sample arm from the detector arm, any errors caused by the detector arm absorbing stray input light can be avoided. Second, since the sample arm is not bilayer, its alignment to the input light source will remain static despite variations in the heat input. Third, due to the lower thermal conductivity of SiNx compared with metals, the absorbed power coming from the sample arm can generate a higher temperature difference, resulting in a thermal detector with a higher sensitivity. Once again, the platform developed in this invention is compatible with different cantilever designs, including variations of this particular bi-arm sensor.

The inventive measurement platform described herein enables the measurement of quantitative broadband absorptance spectra on micro and nano scale sized samples. By combining an interferometer with a micro fabricated multi-layered cantilever beam, the broadband absorptance spectrum of a sample can be measured in a single scan using Fourier Transform Spectroscopy. Compared to conventional dispersive spectrometers, this platform fundamentally allows for faster data acquisition, greater spectral resolution and a higher signal-to-noise ratio. In addition, the use of a bilayer cantilever as the principle thermal sensor enables direct and quantitative measurement of absorptance spectra with picowatt sensitivity. Thus this platform is one of the few capable of characterizing micro- and even nanometer-sized samples. Given the inherent robustness of this platform, it is believed that such a system can be easily integrated into existing FTIR or FTVIS systems as an accessory.

Although the present invention has been shown and described with respect to several preferred embodiments thereof, various changes, omissions and additions to the form and detail thereof, may be made therein, without departing from the spirit and scope of the invention.

What is claimed is:

1. A system for measuring the absorption spectrum of a sample comprising:
    a broadband light source that produces broadband light defined within a range of an absorptance spectrum;
    an interferometer that modulates the intensity of the broadband light source for a range of modulation frequencies;
    a bi-layer cantilever probe arm that is thermally connected to a sample arm having a plurality layers of materials, the broadband light modulated by the interferometer is directed towards the sample and absorbed by the sample and converted into heat, which causes a temperature rise and bending of the bi-layer cantilever probe arm; and
    a detector mechanism that measures and records the deflection of the probe arm so as to obtain the absorptance spectrum of the sample.

2. The system of claim 1, wherein the probe arm comprises different layers of materials having different thermal expansion coefficients.

3. The system of claim 1, wherein the detector mechanism measures the deflection of the probe arm by reflecting a laser beam off the probe arm onto a position sensitive detector, and the output voltage is recorded in a data acquisition system.

4. The system of claim 1, wherein the probe arm is used in background spectrum calibration to correct for variations in the spectral intensity of the light source and atmospheric absorption.

5. The system of claim 1, wherein the probe arm is used to characterize a beam intensity profile and power incident on the sample.

6. The system of claim 1, wherein the probe arm is used for power calibration relating an oscillating displacement amplitude on a position sensitive detector to the absorbed power of the sample.

7. The system of claim 1, wherein the broadband light source comprises plurality of the wavelengths in the x-ray, ultraviolet, visible, infrared, microwaves, or radio waves spectrum.

8. The system of claim 1, wherein the interferometer comprises a Michelson interferometer, Mach-Zender interferometer, Sagnac interferometer, Bath interferometer, or Fabry-Perot interferometer.

9. The system of claim 1, wherein the sample arm comprises a plurality of the materials.

10. The system of claim 9, wherein the materials comprises one or several of the following Si, SiNx, or SiOx.

11. The system of claim 1, wherein the probe arm comprises at least one dielectric layer and one metal layer.

12. The system of claim 1, wherein the probe arm comprises at least one semiconducting layer and one metal layer.

13. A method of measuring the absorption spectrum of a sample comprising:
    producing broadband light defined within a range of an absorptance spectrum using a broadband light source;
    modulating the intensity of the broadband light source for a range of modulation frequencies using an interferometer;
    providing a bi-layer cantilever probe arm that is thermally connected to a sample arm having a plurality of layers of materials, the broadband light modulated by the interferometer is directed towards the sample and absorbed by the sample and converted into heat, which causes a temperature rise and bending of the bi-layer cantilever probe arm; and
    measuring and recording the deflection of the probe arm so as to obtain the absorptance spectrum of the sample.

14. The method of claim 13, wherein the probe arm comprises different layers of materials having different thermal expansion coefficients.

15. The method of claim 13, wherein the detector mechanism measures the deflection of the probe arm by reflecting a laser beam off the probe arm onto a position sensitive detector, and the output voltage is recorded in a data acquisition method.

16. The method of claim 13, wherein the probe arm is used in background spectrum calibration to correct for variations in the spectral intensity of the light source and atmospheric absorption.

17. The method of claim 13, wherein the probe arm is used to characterize a beam intensity profile and power incident on the sample.

18. The method of claim 13, wherein the probe arm is used for power calibration relating an oscillating displacement amplitude on a position sensitive detector to the absorbed power of the sample.

19. The method of claim 13, wherein the broadband light source comprises plurality of the wavelengths in the x-ray, ultraviolet, visible, infrared, microwaves, or radio waves spectrum.

20. The method of claim 13, wherein the interferometer comprises a Michelson interferometer, Mach-Zender interferometer, Sagnac interferometer, Bath interferometer, or Fabry-Perot interferometer.

21. The method of claim 13, wherein the sample arm comprises a plurality of the materials.

22. The method of claim 21, wherein the materials comprises one or several of the following Si, SiNx, or SiOx.

23. The method of claim 13, wherein the probe arm comprises at least one dielectric layer and one metal layer.

24. The method of claim 13, wherein the probe arm comprises at least one semiconducting layer and one metal layer.

* * * * *